United States Patent [19]

Brian et al.

[11] Patent Number: 5,681,743
[45] Date of Patent: Oct. 28, 1997

[54] PLATE ASSEMBLY USEFUL FOR MICROBIOLOGICAL LABORATORY PROCEDURES

[75] Inventors: Barry B. Brian, Oakridge; Larry A. Franchere, Sparta, both of N.J.

[73] Assignee: Becton Dickinson and Company, Franklin Lakes, N.J.

[21] Appl. No.: 504,885

[22] Filed: Jul. 20, 1995

[51] Int. Cl.$^6$ .................................................. C12M 1/22
[52] U.S. Cl. ........................ 435/305.3; 435/305.4; 422/102; 220/335; 206/45.23
[58] Field of Search ........................ 435/288.3, 288.4, 435/305.1, 305.2, 305.3, 305.4; 220/335; 206/45.23; 422/102

[56] References Cited

U.S. PATENT DOCUMENTS

| 442,434 | 12/1890 | Harmer | 206/45.23 |
|---|---|---|---|
| 636,950 | 11/1899 | Butcher | 220/335 |
| 1,850,887 | 3/1932 | Laumonier | 206/45.23 |
| 1,989,159 | 1/1935 | Shiffman et al. | 206/45.23 |
| 2,200,404 | 5/1940 | Vogt | 206/45.23 |
| 2,314,245 | 3/1943 | Rathbun | 220/335 |
| 3,272,379 | 9/1966 | Driza et al. | 220/335 |
| 4,349,632 | 9/1982 | Lyman et al. | 435/305.2 |
| 4,728,607 | 3/1988 | Dorn et al. | 435/305.1 |
| 4,819,794 | 4/1989 | Silverstein et al. | 220/335 |
| 5,339,950 | 8/1994 | Li | 206/45.23 |
| 5,489,039 | 2/1996 | Brownlie et al. | 220/335 |

FOREIGN PATENT DOCUMENTS

| 0053577 | 6/1982 | European Pat. Off. | 220/335 |
|---|---|---|---|
| 4-352649 | 12/1992 | Japan | 220/335 |
| 5-132070 | 5/1993 | Japan | 220/335 |

OTHER PUBLICATIONS

Catalog – Cole–Parmer Instruments, Niles, IL (1994) Table of Contents.
Catalog – Thomas Scientific, Swedesboro, NJ (1993) Table of Contents.
*ELISA in the Clinical Microbiology Laboratory*, ed. by Wreghitt and Morgan–Capner, Public Health Laboratory Service, London, (1990), pp. 6–21.

*Primary Examiner*—William H. Beisner
*Attorney, Agent, or Firm*—Susan A. Capello; Arthur D. Dawson

[57] ABSTRACT

A well plate assembly useful for laboratory-scale cell culture and diagnostic tests of the present invention includes a substantially planar base with at least one well and a top surface. A lid is joined to the base by a hinge as part of the assembly. The hinge allows the lid to be moved between a closed position, where the lid covers the top surface, and a plurality of open positions where the top surface is uncovered. The assembly includes provisions for releasably retaining the lid in the closed and plurality of open positions.

13 Claims, 7 Drawing Sheets

PLATE ASSEMBLY USEFUL FOR MICROBIOLOGICAL LABORATORY PROCEDURES

FIELD OF INVENTION

The present invention relates to an assembly useful for microbiological laboratory procedures and culturing cells, and more particularly relates to a covered multiwell plate for various assays and cell cultures.

BACKGROUND

Well assay plates are widely used in many microbiological and molecular biological procedures. Representative procedures where well plates are used include tissue culture, immuno assays, enzyme linked immunosorbent assays (ELISA) and enzyme immuno assay (EIA) and the like.

In most of these procedures, the plates used have more than one well. Plates having 6, 12, 24 and 96 wells are commercially available from supply houses such as Cole-Parmer Instruments, Niles, Ill. and Thomas Scientific, Swedesboro, N.J. The well plates are available with wells having flat, conical (pointed) or rounded bottoms in capacities ranging from several milliliters (ml) to less than about 0.5 ml. Plates with flat bottom wells are often specified where instrumental or microscopic examination of the well contents from below the surface of the plate is included as part of the procedure.

An example of use of a multiwell plate is seen in several protocols from a reference text entitled "ELISA in the Clinical Microbiology Laboratory" edited by Wreghitt and Morgan-Capner published by Public Health Laboratory Service, London, (1990) on pages 6–21. The protocols describe competitive and non-competitive ELISA for the detection of antigens and antibodies. The authors suggest that multiwell microtiter plates are preferred for these assays. Each of the procedures requires several additions of aqueous solutions, e.g., antibody, antigen specific reagent, enzyme, enzyme substrate and sample. Each addition is followed by a wash step. Thus in one procedure, there may be six or more additions and removals of small amounts of fluid from each well of the microtiter plate. The authors further caution that the operator must ensure that the well is filled with wash fluid and that the wells are completely emptied at the end of each wash cycle. Micropipets are commonly used for the additions and withdrawals of the reagent and wash fluids. Additionally, an operator must avoid cross contamination of the wells and plates as well as keep track of the reagents and equipment being used for each step of the procedure.

The commercially available plates address many of the needs of the users of microtiter plates. Plates are available with several numbers of wells of several sizes. Separate covers are also available for some of the commercially available plates. Most of the commercially available plates are considered to be single use and disposable. They are also supplied pre-sterilized in individual packages. Laboratory workers generally need to be careful not to commingle the lids from one plate to another during manipulations and fluid transfers with the plates.

When well plates are not intended for use in subsequent instrumental procedures, plates having wells with round or conical bottoms are generally used to facilitate removal of fluid with micropipets. The rounded or pointed well bottoms make it easier for a laboratory worker to remove substantially all of the liquid from the well between each step of a multi-step procedure like the example cited above. In cases where subsequent use of an instrument is planned that requires the use of a flat bottom well, laboratory workers often have difficulty in removing substantially all the liquid from the well. An adjustable microplate tilting stand is available from PGC Scientifics Corp., Frederick, Md. that allows users of multi-well plates to position the plate tilted at an angle from a horizontal bench surface to facilitate fluid additions and withdrawals from the wells. Since many procedures utilizing multiwell plates are conducted in laminar flow hoods to avoid contamination, bench space is often at a premium. The available plates and accessories enable laboratory workers to conduct studies, but the efficiency of many laboratory procedures would be further advanced by a well plate with an attached lid that could be utilized to support the plate at an angle to the laboratory bench without the need for additional equipment such as stands, etc. A plate assembly that addresses these needs is described below.

SUMMARY

A well plate assembly of the present invention useful for laboratory scale cell culture and diagnostic testing includes a substantially planar base with at least one well and a top surface. A lid is joined to the base by a hinge as part of the assembly. The hinge allows movement of the lid between a closed position, where the lid covers the top surface, and a plurality of open positions where the top surface is uncovered. The assembly includes provisions for releasably retaining the lid in the closed and open positions.

The lid on the assembly of the present invention may be opened to, and releasably retained in, a position below the plane of the top surface of the base. Thus, a laboratory worker may use the lid, when opened below the plane of the top surface, to support the base at an acute angle to a work surface, facilitating withdrawal of substantially all liquid from the well using a transfer pipet. The support feature substantially eliminates the need for a plate stand in the work area, often an already crowded laminar flow hood, or the need to use one hand to hold and tilt the plate when pipetting the contents of wells. This support feature is particularly useful with plate assemblies having multiple wells with flat bottoms. The assembly of the present invention provides a further benefit to laboratory workers' efficiency by having the attached lid to substantially eliminate cross contamination or sample identification problems caused by mixing-up lids.

DETAILED DESCRIPTION

While this invention is satisfied by embodiments in many different forms, there is shown in the drawings and is herein described in detail several embodiments of the invention with the understanding that the present disclosure is to be considered descriptive of the principles of the present invention and is not intended to limit the scope of the invention to the embodiments illustrated. The scope of the invention is measured by the appended claims and their equivalents.

Figure 1:
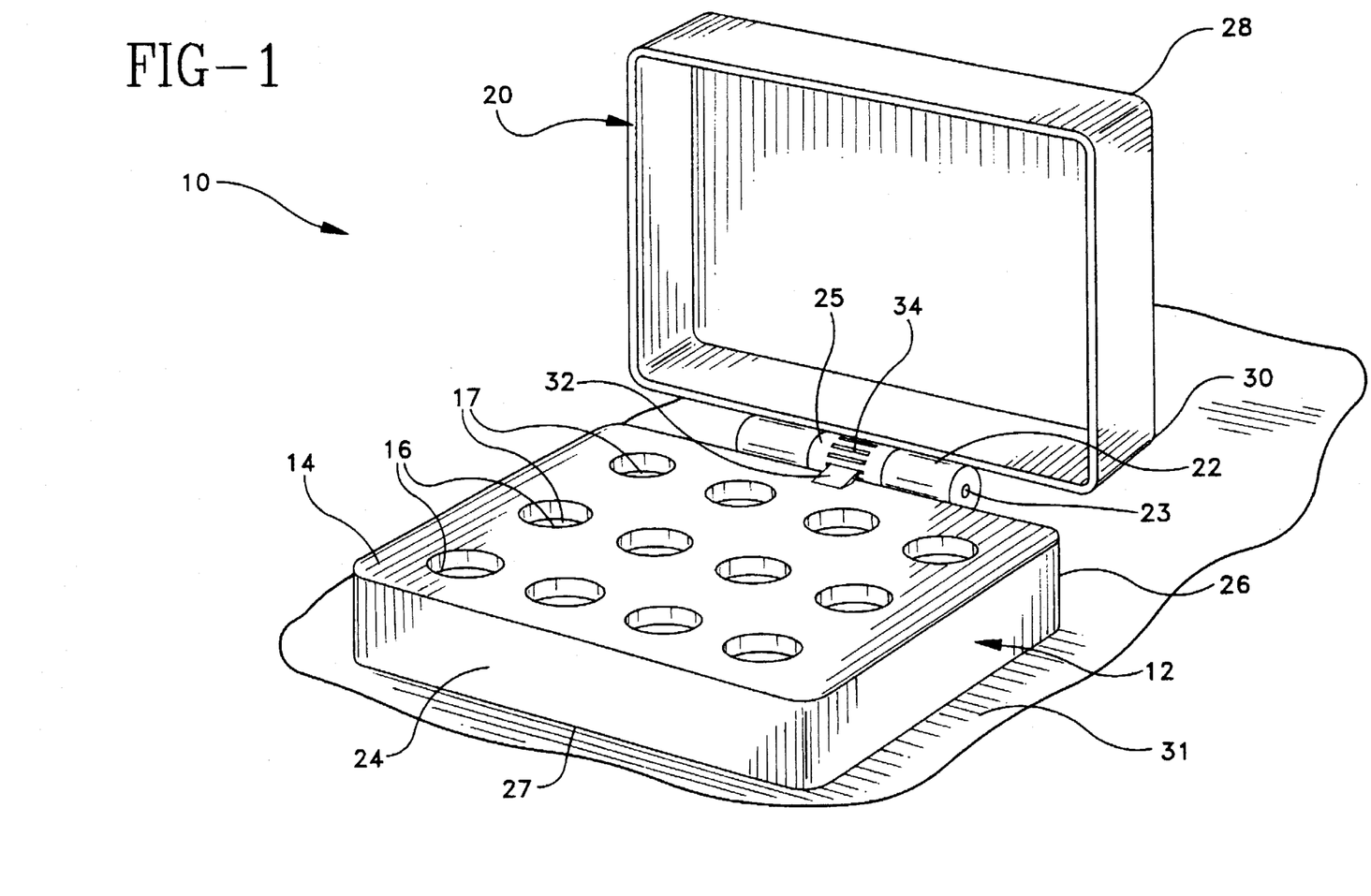
FIG. 1 is a perspective view of the assembly of the preferred embodiment of present invention with the lid in one open position.
Figure 2:
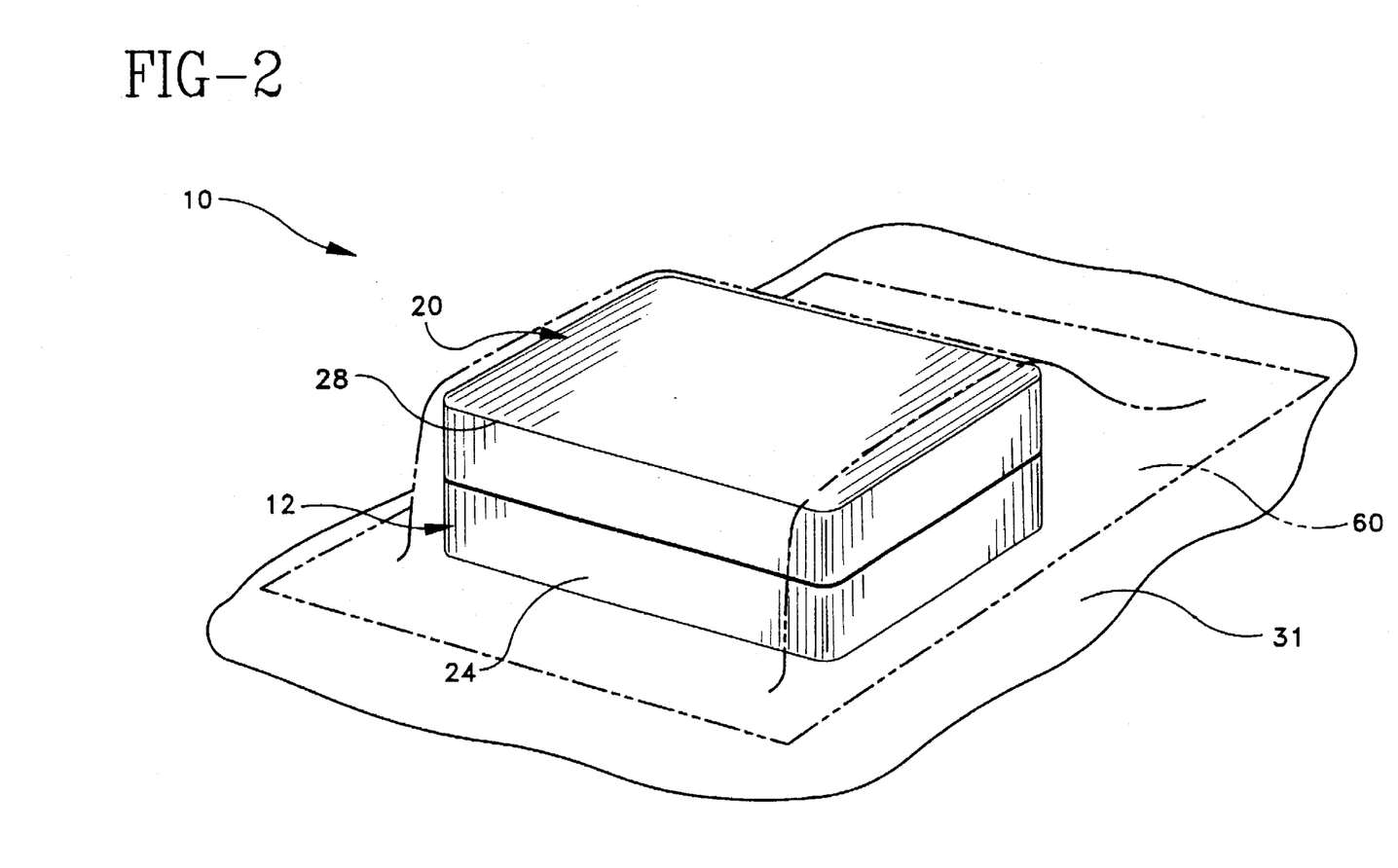
FIG. 2 is a perspective view of the assembly of FIG. 1 with the lid closed.
Figure 3:
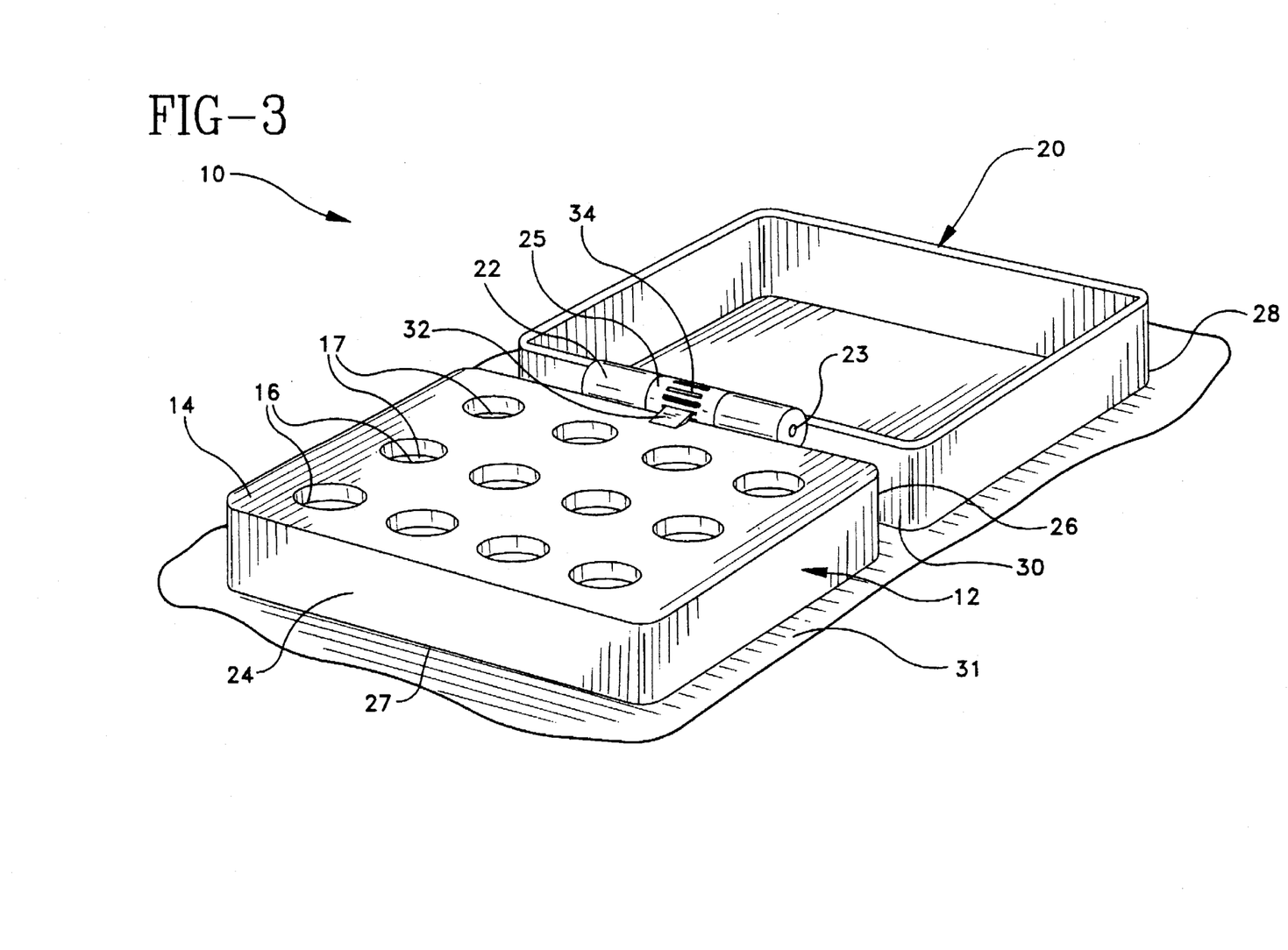
FIG. 3 is a perspective view of the assembly of FIG. 1 with the lid in another open position.
Figure 4:
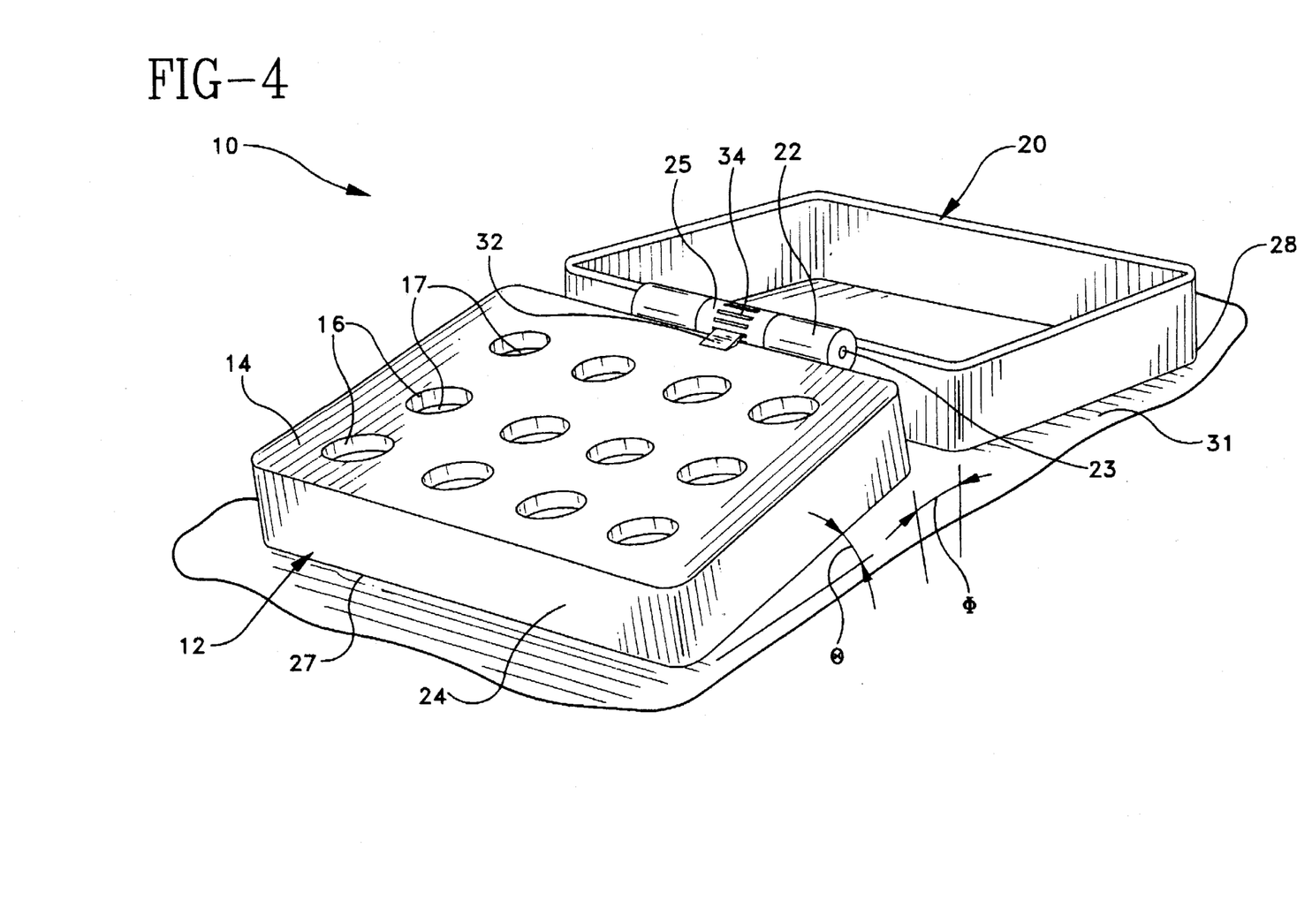
FIG. 4 is a perspective view of the assembly of FIG. 1 with the lid in another open position.

Referring to FIGS. 1–4, a plate assembly 10 of the present invention includes a substantially planar base 12 that has a top surface 14 with at least one well 16 therein. In this description, for convenience, base 12 has twelve wells. The invention is not dependent upon the number of wells in the base. For particular applications, base 12 may include one well or as many more as required. Well 16 is useful for receiving cells for culturing and other laboratory applications. Well 16 has a closed bottom 17 which may be rounded or conical (pointed), but is preferably flat and substantially parallel to the top surface. Assembly 10 further has a lid 20 for covering top surface 14. Lid 20 is joined to base 12 with a hinge 22 having a hinge pin 23 that allows movement of lid 20 between a closed position, as illustrated in FIG. 2, where top surface 14 is covered and a plurality of open positions in which top surface 14 is uncovered, as illustrated in FIGS. 1, 3 and 4. Preferably, when lid 20 is closed and the assembly is positioned on a substantially flat work surface 31, such as a lab bench, top surface 14 is substantially planar and parallel to the flat surface.

Preferred base 12 includes a front 24 and a back 26. Lid 20 preferably has a first edge 28 and a second edge 30, with hinge 22 preferably joining second edge 30 to back 26 of the base so that when lid 22 is in the closed position, as shown in FIG. 2, first edge 30 is substantially aligned with front 24 of the base. In the preferred assembly, base 12 also includes a protuberance 32 and a plurality of depressions 34 associated with lid 20 on a portion 25 of the hinge that moves with the lid. Protuberance 32 is located on base 12 relative to depressions 34 so that protuberance 32 engages one depression in each of the of the positions of lid 20. When protuberance 32 engages one of the depressions 34 it preferably serves as a releasable detent to retain the lid in the selected position relative to base 12.

Preferred assembly 10 also includes at least one open position, as shown in FIG. 4, where lid 20 is pivoted about hinge 22 below the plane of top surface 14. Protuberance 32 preferably engages one of the depressions 34 and releasably retains lid 20 in this position. When the lid is in the open position illustrated in FIG. 4 top surface 14 forms an acute angle Φ with the lid. When the preferred assembly is this open position and placed on work surface 31 so that only a bottom 27 of the base front and lid first edge 28 contact the work surface, the assembly is supported so that base 12 forms an acute angle θ with the work surface. When preferred assembly 10 is in this position, a laboratory worker is easily able to withdraw substantially all liquid from well 16 with a pipet, generally without having to reposition the pipet in the well. This enables the worker to remove substantially all of the fluid from the preferred well with the substantially flat bottom 17 that is substantially parallel to the top surface. Repositioning the pipet in the well may disrupt growth on the surface of the well. Additionally, the worker may more easily judge the amount of wash solution or reagent being added to one well by comparing a meniscus for the fluid being added or withdrawn to a meniscus in an adjoining well without having to prop up the plate on an accessory stand or pick it up to tilt it.

If, as is the case for many procedures, there is an incubation time required between the addition and withdrawal of a fluid, the worker simply closes the lid and sets the assembly aside. The present invention allows the worker to close the lid without having to find the correct lid or needing to worry about the correct alignment of the lid with the base. This reduces the time to conduct the procedure and substantially eliminates an opportunity for cross-contamination or sample mis-identification by incorrectly placing the lid or using the wrong lid.

Figure 5A:
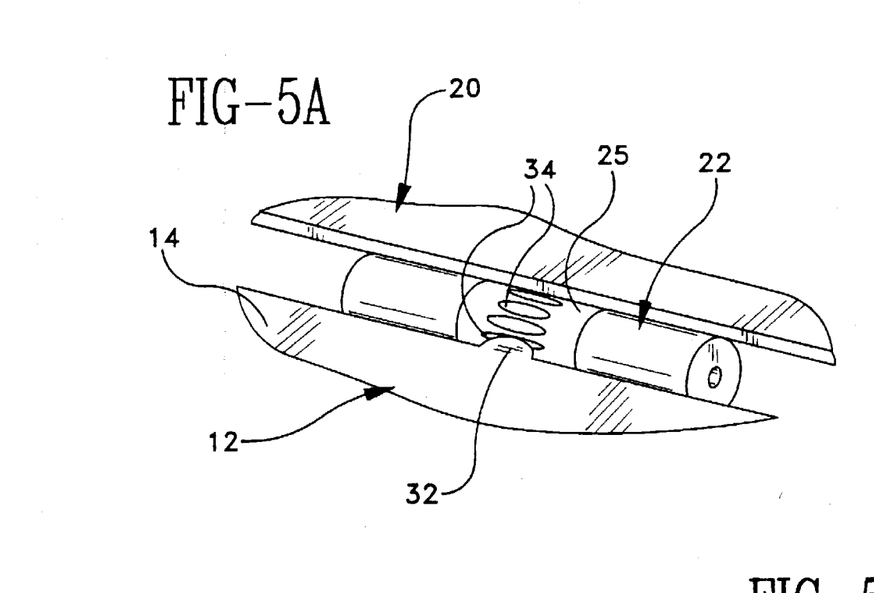
FIG. 5A is a schematic enlarged detail of a hinge area of the assembly of FIG. 1.

FIG. 5A is a schematic enlargement of the hinge area of the preferred embodiment showing the preferred single strip hinge with protuberance 32 and depressions 34 in more detail. Preferably protuberance 32 is on base 12, with depressions 34 being on portion 25 of hinge 22 which rotates as lid 20 moves from one position to another with respect to the base. When protuberance 32 engages depression 34, the engagement substantially holds lid 20 in the position relative to base 12. An alternative to the preferred embodiment (not shown) has a plurality of protuberances on portion 25 engaging a depression on base 12. The function is substantially similar to the preferred embodiment.

Figure 5B:
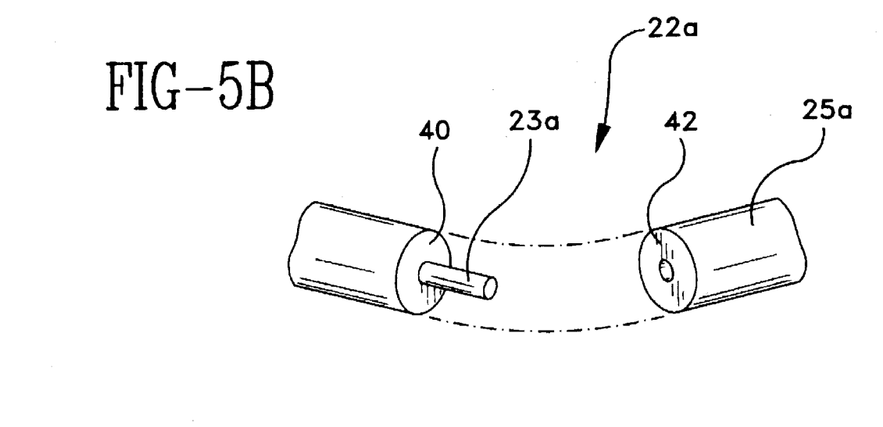
FIG. 5B is an exploded schematic detail of another embodiment of a portion of the assembly of FIG. 1 analogous to FIG. 5A.
Figure 5C:
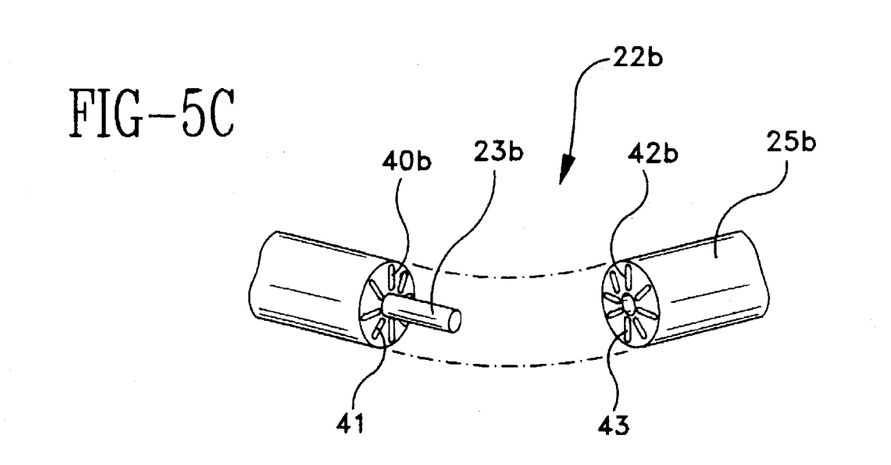
FIG. 5C is an exploded detail of still another embodiment of a portion of the assembly of FIG. 1 analogous to FIG. 5A.
Figure 5D:
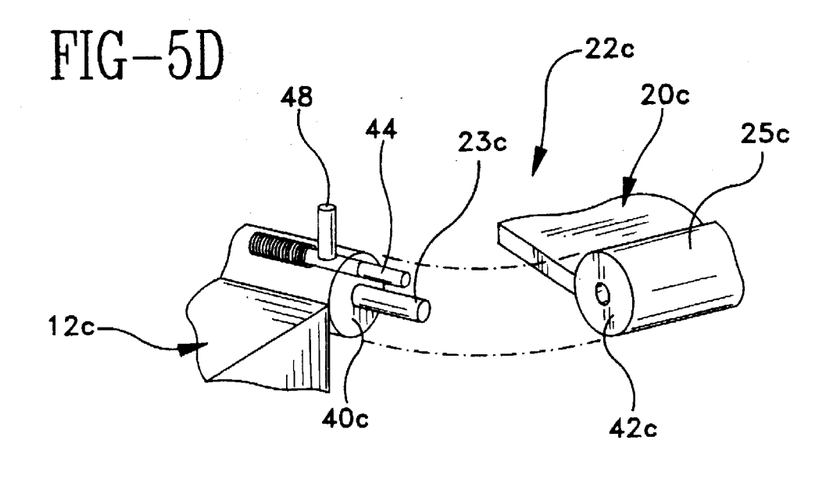
FIG. 5D is an exploded detail of a further embodiment of a portion of the assembly of FIG. 1 analogous to FIG. 5A.

Referring to FIGS. 5B–5D and 6, alternate embodiments of the assembly of the present invention are illustrated. In these alternate embodiments the structure of the assembly is substantially similar to the assembly of FIGS. 1–4 and 5A. Accordingly, substantially similar components of the embodiment are numbered identically to those of the embodiment of FIGS. 1–4 with the exception that a letter suffix is added. FIGS. 5B–5D are schematic exploded enlargements of a portion of the hinge area of the assembly analogous to the area shown in FIG. 5A.

In FIG. 5B, base 12a has a first contact surface 40 as a part of hinge 22a. In this exploded view, hinge pin 23a also is visible. A portion 25a of hinge 22a on lid 20a has a second contact surface 42. In this embodiment, surfaces 40 and 42 are integrally formed with base 12a and lid 20a respectively. Surfaces 40 and 42 are disposed so that they are rotatable in frictional contact with each other as lid 20a is moved relative to base 12a. The frictional contact provides a resistance to opening and closing movement of lid 20a relative to the base and retains lid 20a in a position until the resistance is overcome by a force applied by an operator to move the lid.

Referring to FIG. 5C, in another embodiment first contact surface 40b and second contact surface 42b include a plurality of radial conjugate corrugations 41 and 43, respectively. The contact surfaces are disposed so that corrugations 41 and 43 are engaged and move in and out of phase when lid 20b is moved relative to base 12b about hinge 22b. The corrugations provide a plurality of releasably detented positions for retaining lid 20b in position until overcome by a force applied by an operator to move the lid.

FIG. 5D shows another embodiment of the present invention where first hinge surface 40c is part of base 12c and second hinge surface 42c is part of with lid 20c. In this embodiment, surface 40c includes a movable stop 44 biased by a spring 46 to act against second hinge surface 42c. Stop 44 substantially prevents movement of lid 20c relative to base 12c until the bias is overcome by an operator releasing stop 44 by movement of a slide button 48.

Figure 6:
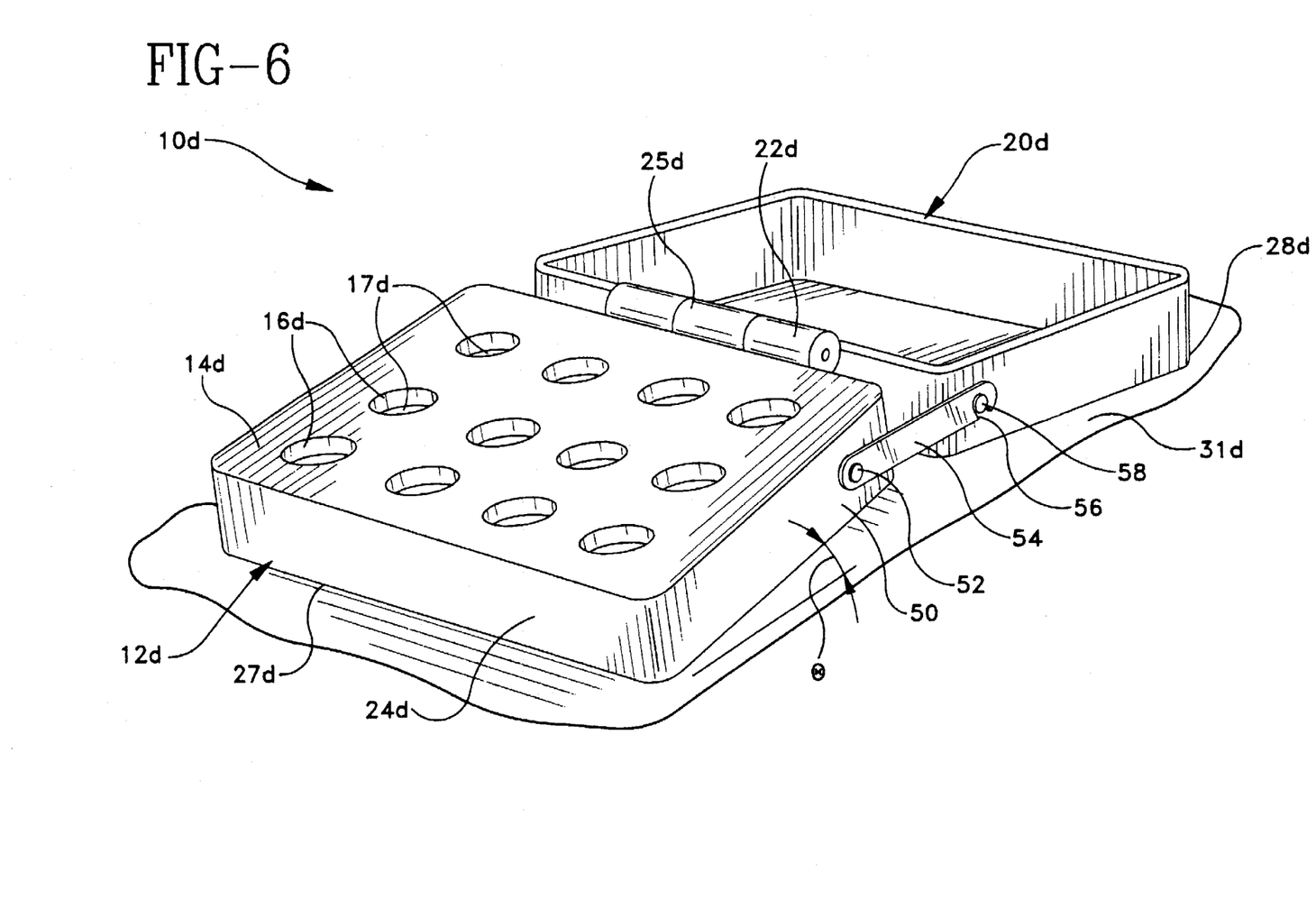
FIG. 6 is a perspective view of an alternative embodiment of the present invention analogous to the view of FIG. 4.

Referring to FIG. 6, base 12d has a sidewall 50 with an pivot 52. An arm 54 is mounted for movement about pivot 52. Arm 54 includes an engagement portion 56 with at least one recess 57. For some applications, it is desirable that portion 56 include more than one recess 57 to engage projection 58, thus providing more than one releasably retained open position. Lid 20d includes a projection 58 for engaging arm 54. Pivot 52 and projection 58 are disposed so that when lid 20d is in an open position below the plane of top surface 14d, arm 54 is movable from one position where engagement portion 56 is free, to another position, as shown in FIG. 6, where recess 57 of engagement portion 56 engages projection 58. In this open position, the engaged arm releasably retains lid 20d in the open position. When lid 20d is in this open position, and assembly 10d is placed on a work surface 31d, only base front bottom 27d and lid first edge 28d contact surface 31d supporting the assembly so that base 12d forms acute angle θ with the surface.

Suitable hinges 22 for joining lid 20 to base 12 include, but are not limited such as a single strip hinge with a pin, a pair of protuberance such as a ball on the other part sized to fit within the socket, hinges formed from interlocking pins and sleeves and the like. The preferred hinge is a strip hinge, as shown in FIGS. 1, 3, 4 and 5A, with pin 23. The particular form of the hinge is not critical to the invention, the hinge serves to join the lid to the base. Other types of hinges in addition to those described above are also satisfactory and are considered within the scope of the invention. Additionally, for particular applications, the scope of the invention includes a hinge that allows the lid to be detached from the base.

Assembly 10 of the present invention may be formed from thermoplastic materials by vacuum forming, sheet molding, injection molding or other similar techniques. Suitable thermoplastic materials include, but are not limited to, polystyrene, polyvinylchloride, polycarbonate, polyethyleneterephthalate and the like. Preferably, assembly 10 is formed from polystyrene by injection molding. Pin 23 may be molded directly into the base or, as shown in FIGS. 1, 3, 4 and 5A, is separate, preferably formed as a separate item from the same or another material and positioned in the hinge during assembly.

Preferably, assembly 10 is sealed in a package 60, shown in phantom in FIG. 2, formed from materials substantially resistant to the passage of microorganisms and then exposed to conditions such as gamma radiation, ethylene oxide and the like, that render any microorganisms present on the assembly substantially non-viable. Thus, the assembly is considered sterile until the package is opened. Suitable materials for package 60 include, but are not limited to paper, nonwovens, formed polymeric sheets, polymeric film and combinations thereof.

The assembly of the present invention provides laboratory workers with a simple easy-to-use plate for small scale cultures and diagnostic testing. The assembly facilitates addition and withdrawal of fluids from the wells on the plate, particularly wells with flat bottoms, without the need for any additional equipment on an already crowded work surface.

What is claimed is:

1. A plate assembly useful for culturing cells comprising:
    a substantially planar base having a top surface and having at least one well therein for receiving cells for culturing, said base having a front portion, a bottom surface and a back portion;
    a lid for covering said top surface and having a first edge and a second edge;
    a hinge connected between said second edge of said lid and said back portion of said base, said hinge allowing movement of said lid between a closed position wherein said first edge of said lid is substantially aligned with said front portion of said base when said lid is in said closed position and said top surface is covered, and a plurality of open positions wherein said top surface is uncovered, said lid being operative to move through an angle of at least 181 degrees relative to said closed position into one of said open positions below a plane of said top surface so that said first edge of said lid is positioned against a support surface underneath said base such that at least a portion of said bottom surface is angled and raised away from the support surface; and
    retention means for releasably retaining said lid in said open positions.

2. The assembly of claim 1 wherein said hinge comprises pivot.

3. The assembly of claim 2 wherein said pivots are selected from the group consisting of a single strip hinge having a pin therethrough, a pair of hinges each comprising a socket and a protuberance fit within said socket and interlocking pins and sleeves.

4. The assembly of claim 1 wherein said retention means comprises a protuberance on said base and a plurality of depressions on said lid disposed to engage releasably, so that when said lid is moved from one of said positions to another of said positions relative to said base, said protuberance disengages from one of said depressions and engages another of said depressions thereby retaining said lid in the position relative to said base.

5. The assembly of claim 1 wherein said retention means comprises a first surface on said base and a second surface on said lid, said surfaces being disposed in rotatable frictional contact with each other thereby providing a resistance to opening and closing movement of said lid relative to said base about said hinge, said resistance thereby retaining said lid in a position until being overcome by a force applied to move said lid.

6. The assembly of claim 5 wherein said first surface and said second surface further each include a plurality of conjugate corrugations disposed and engaged so that said movement of said lid relative to said base causes the corrugations to move in and out of phase with each other thereby providing a plurality of releasably detented positions for opening and closing movement of said lid.

7. The assembly of claim 1 wherein said retention means includes a first hinge surface associated with said base, a second hinge surface associated with said lid and a movable stop on the first hinge surface biased to act against said second hinge surface substantially preventing movement of said lid relative to said base until said bias is overcome to release said stop, thereby retaining said lid in a position relative to said base.

8. The assembly of claim 1, wherein said base further includes a side wall having a pivot and wherein said retention means comprises:
    an arm mounted for movement about said pivot having an engagement portion; and
    said lid having a side wall having a projection thereon, said pivot and said projection being disposed so that when said lid is in an open position below the plane of said top surface, said arm is moveable from one position where said engagement portion is free to another position wherein said engagement portion engages said projection on said lid, said lid thereby being releasably retained in said open position.

9. The assembly of claim 1 wherein lid is detachable from said base at said hinge.

10. The assembly of claim 1 wherein said well has a substantially flat bottom substantially parallel to said top surface.

11. The assembly of claim 1 wherein said base has a plurality of wells.

12. The assembly of claim 1 wherein said assembly is contained within a sealed package substantially resistant to the transmission of microorganisms and exposed to an environment rendering any microorganisms therein substantially nonviable.

13. A plate assembly useful for culturing cells comprising:

- a substantially planar base having a top surface, a front, a bottom surface, and a back and having at least one well therein for receiving cells for culturing;
- a lid having a first edge and a second edge;
- a hinge joining said second edge of said lid to said back of said base, said hinge allowing movement of said lid relative to said base between a closed position where said lid first edge is generally aligned with and adjacent to said base front and a plurality of open positions wherein said top surface is uncovered;
- a protuberance on said base and a plurality of depressions on said lid disposed to engage releasably, so that when said lid is moved from one of said positions to another of said positions relative to said base, said protuberance disengages from one of said depressions and engages another of said depressions thereby retaining said lid in a selected position relative to said base; and
- wherein said lid is moveable into at least one said open position wherein said lid is at an angle of at least 181 degrees relative to said closed position and is below a plane containing said base bottom surface such that said lid first edge is in supporting engagement with a support surface beneath said assembly and at least a portion of said bottom surface is angled and removed from the support surface.

\* \* \* \* \*